(12) United States Patent  
Teles et al.

(10) Patent No.: US 8,461,392 B2
(45) Date of Patent: Jun. 11, 2013

(54) PROCESS FOR PREPARING CYCLIC KETONES

(75) Inventors: Joaquim Henrique Teles, Otterstadt (DE); Wilhelm Ruppel, Mannheim (DE); Ulrike Wegerle, Worms (DE); Anton Meier, Birkenheide (DE); Thomas Genger, Lambsheim (DE); Michael Schelper, Ludwigshafen (DE); Peter Resch, Hettenleidelheim (DE)

(73) Assignee: BASF SE, Ludwigshafen (DE)

( * ) Notice: Subject to any disclaimer, the term of this patent is extended or adjusted under 35 U.S.C. 154(b) by 90 days.

(21) Appl. No.: 13/060,545

(22) PCT Filed: Aug. 26, 2009

(86) PCT No.: PCT/EP2009/060956
§ 371 (c)(1),
(2), (4) Date: Feb. 24, 2011

(87) PCT Pub. No.: WO2010/023211
PCT Pub. Date: Mar. 4, 2010

(65) Prior Publication Data
US 2011/0152576 A1     Jun. 23, 2011

(30) Foreign Application Priority Data
Aug. 29, 2008   (EP) .................................... 08163319

(51) Int. Cl.
   *C07C 45/78*     (2006.01)
(52) U.S. Cl.
   USPC .......................................... 568/363; 568/375

(58) Field of Classification Search
   USPC .................................................. 568/375, 363
   See application file for complete search history.

(56) References Cited

U.S. PATENT DOCUMENTS

| 4,806,692 | A | 2/1989 | Yamada et al. |
| 7,105,704 | B2 | 9/2006 | Panov et al. |
| 7,282,612 | B2 | 10/2007 | Panov et al. |
| 2005/0203316 | A1 | 9/2005 | Panov et al. |
| 2010/0179352 | A1 | 7/2010 | Teles et al. |

FOREIGN PATENT DOCUMENTS

| GB | 649680 A | 1/1951 |
| RU | 2002106986 A1 | 5/2006 |
| WO | WO-98/15514 A1 | 4/1998 |
| WO | WO-03/078370 A1 | 9/2003 |
| WO | WO-03/078371 A1 | 9/2003 |
| WO | WO-03/078372 A1 | 9/2003 |
| WO | WO-03/078374 A1 | 9/2003 |
| WO | WO-03/078375 A1 | 9/2003 |
| WO | WO-2004/000777 A1 | 12/2003 |
| WO | WO-2008/148661 A1 | 12/2008 |

OTHER PUBLICATIONS

F.S. Bridson-Jones, et al., "Oxidation of organic compounds by nitrous oxide. Part I," Journal of the Chemical Society, 1951, pp. 2999-3008.

*Primary Examiner* — Sikarl Witherspoon
(74) *Attorney, Agent, or Firm* — Novak Druce Connolly Bove + Quigg LLP

(57) ABSTRACT

The present invention relates to a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein said reaction is performed adiabatically.

18 Claims, 3 Drawing Sheets

PROCESS FOR PREPARING CYCLIC KETONES

CROSS-REFERENCE TO RELATED APPLICATIONS

Figure 1:
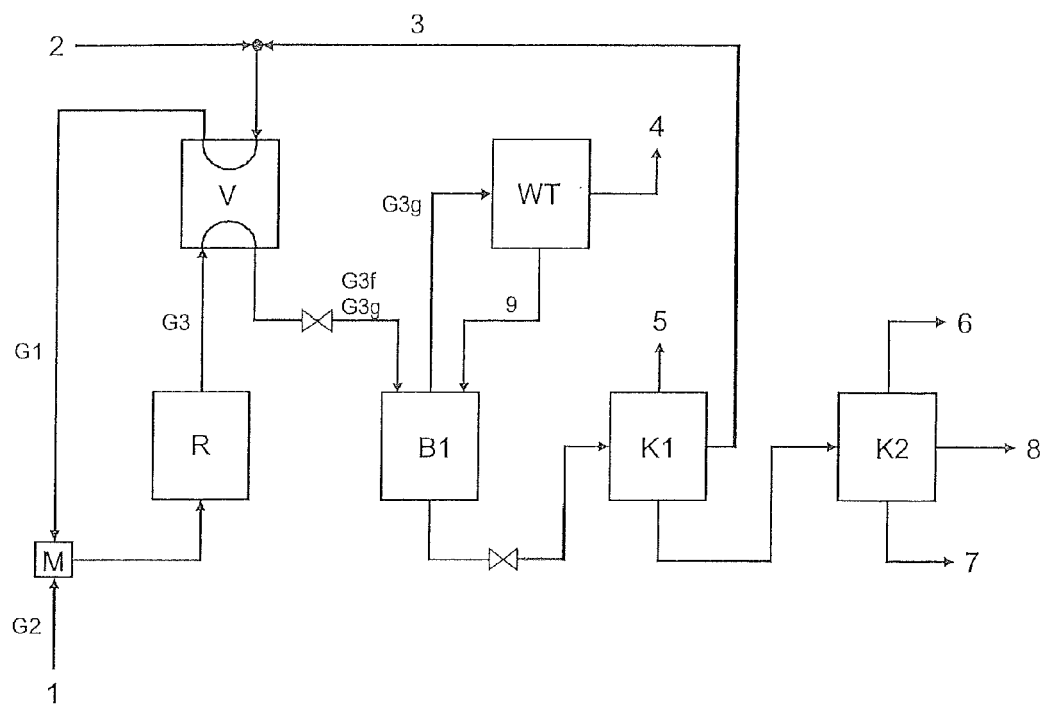

This application is a national stage application (under 35 U.S.C. §371) of PCT/EP2009/060956, filed Aug. 26, 2009, which claims benefit of European application 08163319.0, filed Aug. 29, 2008.

BACKGROUND OF THE INVENTION

The present invention relates to a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide ($N_2O$), wherein said reaction is performed adiabatically.

Processes for preparing cyclopentanone are known in principle from the prior art. It is likewise known that cyclopentanone can be obtained by reacting cyclopentene with dinitrogen monoxide. The preparation of cyclopentanone by oxidation of cyclopentene with dinitrogen monoxide is a very selective reaction which is strongly exothermic.

For instance, GB 649,680 discloses the reaction of alkenes, for example cyclohexene, with dinitrogen monoxide in order to obtain the corresponding cyclic ketones, for example cyclohexanone. The reaction is performed at a temperature of from 200 to 300° C. and a pressure of from 100 to 500 bar in the liquid phase. The document cited does not disclose that cyclic olefins are reacted with dinitrogen monoxide under adiabatic conditions.

F. S. Bridson-Jones et al. describe, in J. Chem. Soc., p. 2999-3008 (1951), the reaction of olefins with dinitrogen monoxide, which converts, for example, cyclohexene to cyclohexanone. The process according to this document is performed at a temperature of, for example, 300° C. and a pressure of 500 bar in an autoclave. F. S. Bridson-Jones et al. do not disclose that cyclic olefins can be reacted with dinitrogen monoxide under adiabatic conditions.

The synthesis of carbonyl compounds from alkenes with dinitrogen monoxide is also described in various international patent applications. For instance, WO 03/078370 discloses a process for preparing carbonyl compounds from aliphatic alkenes with dinitrogen monoxide. The reaction is performed at temperatures in the range from 20 to 350° C. and pressures from 0.01 to 100 bar. WO 03/078374 discloses a corresponding process for preparing cyclohexanone. According to WO 03/078372, cyclic ketones having from 4 to 5 carbon atoms are prepared. According to WO 03/078375, cyclic ketones are prepared under these process conditions from cyclic alkenes having from 7 to 20 carbon atoms. WO 03/078371 discloses a process for preparing substituted ketones from substituted alkenes. WO 04/000777 discloses a process for reacting di- and polyalkenes with dinitrogen monoxide to give the corresponding carbonyl compounds. No adiabatic process for preparing cyclic ketones from the corresponding cyclic olefins is disclosed in the international applications cited.

U.S. Pat. No. 4,806,692 discloses a process for preparing oxygen-comprising organic compounds from olefins; more particularly, the oxidation of cyclic olefins under mild conditions is disclosed, in order to obtain corresponding cyclic ketones. According to U.S. Pat. No. 4,806,692, such an oxidation is effected in the presence of palladium catalysts at a temperature of 80° C. or lower and atmospheric pressure. U.S. Pat. No. 4,806,692 does not disclose a process for preparing cyclic ketones from the corresponding cyclic olefins by reaction with dinitrogen monoxide under adiabatic conditions.

U.S. Pat. No. 7,282,612 B2 discloses a process for preparing monocyclic ketones having 4 or 5 carbon atoms by reacting the corresponding cyclic alkenes having 4 or 5 carbon atoms with dinitrogen monoxide, if appropriate in a mixture with an inert gas at a temperature of from 20 to 300° C. and a dinitrogen monoxide pressure of from 0.01 to 10 bar. No adiabatically performed process is disclosed in U.S. Pat. No. 7,282,612 B2.

RU 2002106986 discloses a process for preparing monocyclic ketones having 4 or 5 carbon atoms by oxidation of cyclobutene or cyclopentene with dinitrogen monoxide, likewise at a dinitrogen monoxide pressure of from 0.01 to 100 bar and a temperature of from 20 to 300° C.

The reaction of monocyclic olefins with dinitrogen monoxide in order to obtain the corresponding ketones is strongly exothermic. In addition, mixtures of dinitrogen monoxide with organic compounds having a high concentration of dinitrogen monoxide pose an explosion risk. It is therefore necessary for a corresponding prior art process to provide complicated and costly apparatus for heat removal from the exothermic reaction. Furthermore, the reactors have to be designed for the high pressures and temperatures.

BRIEF SUMMARY OF THE INVENTION

It is thus an object of the present invention to provide a process for preparing monocyclic ketones having from 4 to 20 carbon atoms, which is notable in that no complicated and hence costly apparatus has to be provided.

It is a further object of the present invention to provide a corresponding process with which monocyclic ketones, especially cyclopentanone and/or cyclohexanone, are obtainable in high yield and maximum purity.

According to the invention, these objects are achieved by a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein said reaction is performed adiabatically.

A BRIEF DESCRIPTION OF THE FIGURE

FIG. 1 illustrates a pilot plant according to the invention.

DETAILED DESCRIPTION OF THE INVENTION

In the context of the present invention, an adiabatic reaction is understood to mean a reaction in which essentially no heat exchange takes place between reactor contents and environment during the reaction. In the context of the present invention, an adiabatic reaction is preferably understood to mean a reaction in which preferably less than 10%, more preferably less than 5%, of the heat generated is released to the environment.

Processes known to date for preparing cyclic ketones from the corresponding olefins and dinitrogen monoxide have the disadvantage that, as a result of the strongly exothermic reaction of olefin and dinitrogen monoxide, a large amount of heat is generated, which has to be removed from the reaction mixture, i.e. from the reactor in which the reaction takes place. This leads to high material costs and hence capital costs for the reactor. A simple design in construction terms of the reactor for preparing monocyclic ketones from the corresponding olefins and dinitrogen monoxide has not been possible to date.

It has been found that the problem described can be solved by performing the strongly exothermic reaction adiabatically, i.e. the heat generated during the reaction remains essentially in the system and is not removed to the outside. By virtue of the heat of reaction generated during the reaction remaining in the system, the reactor construction and the process regime are simplified very significantly, since cooling and heat-dispersing elements do not have to be implemented in the reactor by construction means.

In a preferred embodiment, the process according to the invention is performed by reacting mixtures G1 and G2 in a reactor thermally insulated from the environment, wherein the thermal energy generated in the exothermic reaction remains essentially within the reactor and is not removed to the outside.

According to the invention, the heat of reaction generated can preferably be established through the conversions of the individual reactants. The conversions of the individual reactants can in turn be influenced by the residence time, by the inlet temperature of the reactant mixture ($T_{in}$), by the reaction pressure and by the concentration of the individual reactants in the reactant mixture. It is thus possible in accordance with the invention, for example through selection of the parameters mentioned in conjunction with a suitable reactor, to perform the process adiabatically, i.e. essentially without supply of thermal energy to and/or removal of thermal energy from the reaction mixture within the reactor.

In an adiabatic process regime, the difference between the temperature of the products ($T_{out}$) and the temperature of the reactants ($T_{in}$) is defined as the adiabatic temperature increase ($T_{adiab}$). In a preferred embodiment of the process according to the invention, $T_{adiab}$ is between 10 and 140° C., more preferably between 20 and 125° C. and most preferably between 25 and 100° C.

In a preferred embodiment, the present invention accordingly also relates to a process as described above for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein the adiabatic temperature increase in the reactor is between 10 and 140° C., more preferably between 20 and 125° C. and most preferably between 25 and 100° C.

In a preferred embodiment, the process according to the invention can be performed in such a way that the abovementioned parameters are established such that the heat of reaction generated by the reaction is the heat which is needed in order that the production mixture leaves the reactor with a temperature ($T_{out}$) which is still significantly below the onset temperature for the decomposition thereof. In the context of the present invention, the onset temperature is defined as the temperature from which a significant exothermic reaction is recorded in a differential scanning calorimetry test (DSC test) of the product mixture with a rate of temperature increase of at least 0.1 K/min.

In a preferred embodiment, the present invention accordingly also relates to a process as described above for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein the reactor outlet temperature is below the onset temperature for the decomposition of the product mixture.

In a particularly preferred embodiment, the process according to the invention can be performed in such a way that the abovementioned parameters are established such that the heat of reaction generated by the reaction is the heat which is needed in order that the product mixture leaves the reactor with a temperature ($T_{out}$) which is at least 10 K below the temperature at which the adiabatic induction time is exactly 24 hours. The adiabatic induction time as a function of temperature can be derived in a manner known per se from the data of DSC experiments with different heating rates.

In a preferred embodiment, the present invention accordingly also relates to a process as described above for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein the reactor outlet temperature is at least 10 K below the temperature at which the adiabatic induction time of the product mixture is 24 hours.

It is possible in accordance with the invention that both reactants, i.e. the at least one monocyclic olefin having from 4 to 20 carbon atoms and dinitrogen monoxide, have the same inlet temperature or different inlet temperatures. What is relevant in the context of the present invention is the reactor inlet temperature of the reactant mixture, i.e. the temperature which is established when all reactant streams are mixed together.

In a preferred embodiment of the invention, the reactor inlet temperature of the reactant mixture ($T_{in}$) is from 170 to 270° C., more preferably from 200 to 260° C., for example from 220 to 250° C.

In a preferred embodiment, the present invention accordingly also relates to a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein said reaction is performed adiabatically and the reactor inlet temperature of the reactant mixture ($T_{in}$) is from 170 to 270° C.

The temperature that the reactants have at the reactor inlet preferably also corresponds to the minimum temperature at which, in the process according to the invention, the desired conversion can still be achieved in an industrially implementable reactor size. The minimum temperature at which, in the process according to the invention, the desired conversion can still be achieved in an industrially realizable reactor size is therefore generally at least 170° C., preferably at least 200° C.

The maximum reactor outlet temperature ($T_{out}$) of the product mixture at which the process according to the invention can be performed is generally at most 340° C., preferably at most 320° C., more preferably at most 300° C. According to the invention, the maximum reactor outlet temperature ($T_{out}$) is selected such that preferably no thermal decomposition of the product formed or of the unconverted reactants takes place.

The process according to the invention is thus generally performed at a temperature of from 170 to 340° C., preferably from 200 to 320° C., the former temperature being the reactor inlet temperature ($T_{in}$) of the reactant mixture and the latter temperature the reactor outlet temperature ($T_{out}$) of the product mixture.

In a preferred embodiment, the process according to the invention is performed at a reaction pressure of from 60 to 500 bar, more preferably from 80 to 325 bar, more preferably from 90 to 180 bar, for example at from 100 to 150 bar.

In a preferred embodiment, the present invention accordingly also relates to a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein said reaction is performed adiabatically and the reaction pressure is from 60 to 500 bar.

In a further embodiment, the process according to the invention can be performed in such a way that the molar ratio between the substrates, i.e. the at least one monocyclic olefin having from 4 to 20 carbon atoms and dinitrogen monoxide, has a suitable value such that the heat of reaction generated by the reaction is exactly the heat which, given an appropriate reactor inlet temperature ($T_{in}$) of the reactant mixture and given full conversion of the reactant present in deficiency, preferably dinitrogen monoxide, gives rise to a reactor outlet temperature ($T_{out}$) of the product mixture which is below the abovementioned maximum temperatures of 340° C., preferably 320° C., more preferably 300° C.

In a preferred embodiment, the molar ratio between dinitrogen monoxide and the at least one monocyclic olefin is between 0.02 and 0.3, more preferably between 0.05 and 0.25 and most preferably between 0.08 and 0.2. According to the invention, the "molar ratio of the reactants" means the quotient of the amounts of the reactants. Since the amounts of the reactants each bear the unit of "mole", the quotient of these amounts is unitless.

In a preferred embodiment, the present invention accordingly also relates to a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein said reaction is performed adiabatically and the molar ratio between dinitrogen monoxide and the at least one monocyclic olefin is between 0.02 and 0.3, preferably between 0.05 and 0.25.

In a further preferred embodiment, the conversion based on dinitrogen monoxide in the process according to the invention is from 80 to 100%, more preferably from 90 to 99%, most preferably from 90 to 96%.

In a preferred embodiment, the present invention accordingly also relates to a process for preparing at least one monocyclic ketone having from 4 to 20 carbon atoms as described above, wherein the conversion based on dinitrogen monoxide is from 80 to 100%.

In a very particularly preferred embodiment, the present invention also relates to a process for preparing at least one monocyclic ketone having from 4 to 20 carbon atoms by reacting a mixture G1 comprising at least one monocyclic olefin having from 4 to 20 carbon atoms with a mixture G2 comprising at least dinitrogen monoxide, wherein said reaction is performed adiabatically, the process is performed at a temperature of from 170 to 340° C., the reaction pressure is from 60 to 500 bar, the molar ratio between dinitrogen monoxide and the at least one monocyclic olefin is between 0.05 and 0.25 and the conversion based on dinitrogen monoxide is from 80 to 100%.

The process according to the invention can be performed in all reactors which are known to those skilled in the art and are suitable for an adiabatic reaction regime, for example in a tubular reactor. In order to ensure an adiabatic reaction regime, it is, for example, necessary that the reactor is insulated sufficiently from the environment, such that essentially no heat of reaction is released to the environment and is thus no longer available to the actual reaction. In a particularly preferred embodiment, the heat generated by the reaction is discharged from the reactor by the product stream.

It is also possible in accordance with the invention to use a plurality of reactors, which may be connected in parallel or in series.

In a preferred embodiment, the process according to the invention is performed continuously. However, it is also possible in the context of the present invention that the process according to the invention is performed semicontinously or also discontinuously, i.e., batchwise.

The reactor chamber of the reactor usable in accordance with the invention may be empty or may, if appropriate, be segmented by suitable internals. In general, the reactor has a flow profile suitable for an adiabatic reaction. In the reactor for use for the process according to the invention, preferably essentially no backmixing takes place. The reactor preferably has a residence time distribution which corresponds to that of a stirred tank cascade with at least 8 stirred tanks. The reactor more preferably has a residence time distribution which corresponds to that of a stirred tank cascade with at least 12 stirred tanks. The flow profile which is preferred in the process according to the invention for the reaction mixture depends on the reactor used and can, if appropriate, be adjusted accordingly by suitable internals known to those skilled in the art, for example perforated plates, or by filling the reactor with a suitable packed bed.

For the process according to the invention, preference is given to using a tubular reactor with a length to diameter ratio greater than 1. The reactor more preferably comprises at least perforated plates to reduce backmixing.

It is possible in accordance with the invention that the reactor is operated in a recumbent or upright position, preferably upright. The flow of the reaction mixture through an upright reactor may be from the bottom upward or from the top downward. Preference is given to performing the process according to the invention in an upright reactor through which the reaction mixture flows from the bottom upward.

A reactor particularly suitable for the continuous process regime is, for example, a tubular reactor which is preferably sufficiently insulated. Appropriate tubular reactors are known to those skilled in the art.

It is possible in accordance with the invention that the reactant streams, preferably mixture G1 and mixture G2, are fed separately to the reactor. It is also possible and preferred in accordance with the invention that the reactant streams are fed to the reactor in already premixed form.

In a particularly preferred embodiment, the reactant streams, preferably mixture G1 and mixture G2, are mixed in the process according to the invention, for example with the aid of a suitable mixing apparatus, for example a static mixer, upstream of the reactor inlet.

The temperatures of the mixtures G1 and G2 are selected such that the temperature of the mixed reactant stream has the desired temperature $T_{in}$. Particular preference is given to preheating only mixture G1 and to mixing it upstream of the reactor, in a suitable mixing apparatus, with a non-preheated mixture G2, the temperature to which the mixture G1 is heated being selected such that the temperature of the mixed reactant stream corresponds to the desired temperature $T_{in}$.

The reactant streams, preferably mixture G1 and/or G2, more preferably only mixture G1, can be preheated by all processes known to those skilled in the art, before the reaction to give at least one monocyclic ketone having from 4 to 20 carbon atoms, to a temperature of preferably from 170 to 270° C., more preferably from 200 to 260° C., for example from 220 to 250° C., for example by means of an external heat source, for example steam, in a heat exchanger known to those skilled in the art, which functions as a preheater in accordance with the invention. According to the invention, the reactant streams are preheated outside the reactor in a suitable heat exchanger.

The present invention thus also relates to a process as described above, wherein the mixture G1 and/or G2 is preheated to a temperature of from 170 to 270° C. before the reaction to give at least one monocyclic ketone having from 4 to 20 carbon atoms.

In a particularly preferred embodiment of the process according to the invention, at least a portion of the mixture G1 is preheated to an appropriate temperature before it is contacted with mixture G2, preferably just upstream of the reactor or within the reactor. It is thus possible, for example, to prevent the inventive reaction from taking place outside the actual reactor to a significant degree.

In a particularly preferred embodiment of the process according to the invention, the thermal energy needed to preheat the reactant streams is withdrawn at least partly, preferably fully, from the reactor output, i.e. from the hot product stream of the process according to the invention. In a preferred embodiment of the process according to the invention, for this purpose, at least a portion of the product stream is contacted with at least a portion, for example from 70 to 95%, of mixture G1 in a heat exchanger, for example a countercurrent heat exchanger.

According to the invention, the temperature of the stream supplied to the reactor can be adjusted via the proportion of the mixture G1 which is preheated by means of such a heat exchanger.

The present invention thus also relates to a process as described above, wherein the thermal energy needed to preheat mixture G1 and/or G2 is withdrawn at least partly, preferably fully, from the product stream of the process according to the invention.

In a preferred embodiment of the process according to the invention, at least a portion of the product stream is contacted with at least a portion, for example from 70 to 95%, of mixture G1, before the product stream is worked up further.

According to the invention, the product stream obtained from the process has a reactor outlet temperature ($T_{out}$) of generally at most 340° C., preferably at most 320° C. and more preferably at most 300° C. After being contacted with the reactant stream, preferably with mixture G1, the product stream generally has a temperature of from 150 to 220° C., preferably from 170 to 200° C., for example from 180 to 190° C. According to the invention, the reactant stream, preferably mixture G1, is heated to generally from 180 to 280° C., preferably from 240 to 275° C., for example from 250 to 260° C. In a particularly preferred embodiment of the process according to the invention, the mixture G1 which has been preheated to a temperature of generally from 180 to 280° C., preferably from 240 to 275° C., for example from 250 to 260° C., is mixed with mixture G2 so as to result in a temperature of the combined reactant stream, preferably comprising mixture G1 and G2, of preferably from 170 to 270° C., more preferably from 200 to 260° C., for example from 220 to 250° C.

In principle, it is possible in accordance with the invention to use any mixture G1 comprising at least one monocyclic olefin having from 4 to 20 carbon atoms, preferably having from 4 to 8 carbon atoms.

According to the invention, the at least one monocyclic olefin which has from 4 to 20 carbon atoms and is present in the mixture G1 may have one or more carbon-carbon double bond(s). In a preferred embodiment, the at least one monocyclic olefin which has from 4 to 20 carbon atoms and is present in mixture G1 has one carbon-carbon double bond. It is also possible in accordance with the invention that a mixture G1 is used, which, as well as at least one monocyclic olefin having from 4 to 20 carbon atoms with one carbon-carbon double bond, comprises one or more monocyclic olefin(s) having from 4 to 20 carbon atoms with two or more carbon-carbon double bonds.

The mixture G1 used in the process according to the invention more preferably comprises at least one monocyclic olefin selected from the group consisting of cyclobutene, cyclopentene, cyclohexene, cycloheptene, cyclooctene, cyclodecene, cyclotetradecene, cyclopentadecene, cyclohexadecene, cycloeicosene and mixtures thereof. Most preferably, the mixture G1 used in the process according to the invention comprises a monocyclic olefin selected from the group consisting of cyclopentene, cyclohexene, cycloheptene, cyclooctene and mixtures thereof. Cyclopentene (I), cyclohexene (II), cycloheptene (III) and cyclooctene (IV) are depicted below.

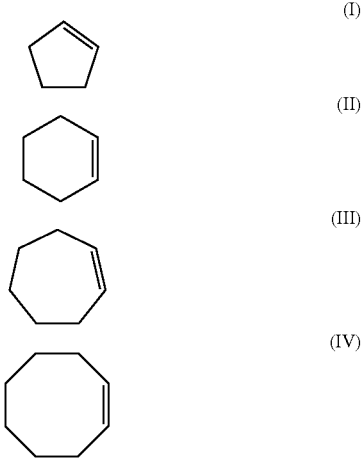

In principle, the mixture G1 may, in addition to cyclopentene, comprise any other compound. Suitable compounds also include those which can likewise react with dinitrogen monoxide ($N_2O$). Preference is given here to those compounds which can in principle react with $N_2O$ but are inert toward $N_2O$ under the reaction conditions selected in accordance with the invention. The term "inert", as used in the context of the present invention, refers to compounds which, under the reaction conditions selected in accordance with the invention, either do not react with $N_2O$ or react with $N_2O$, compared to the reaction of monocyclic olefins having from 4 to 20 carbon atoms, to such a limited degree that their reaction product with $N_2O$ is present in the resulting mixture to an extent of at most 5% by weight, preferably to an extent of at most 3% by weight and more preferably to an extent of at most 2% by weight, based in each case on the total weight of the resulting mixture.

In the process according to the invention, in a preferred embodiment, it is possible to use a mixture G1 which, as well as the at least one olefin having from 4 to 20 carbon atoms, comprises at least one further hydrocarbon.

The term "hydrocarbons", as used in the context of the present invention, refers to compounds of which each is an unsubstituted hydrocarbon and therefore consists only of C and H atoms, for example olefins or saturated hydrocarbons.

In a preferred embodiment, the mixture G1 used comprises, as well as the at least one olefin having from 4 to 20 carbon atoms, at least one further hydrocarbon having from 4 to 20 carbon atoms, for example selected from the group consisting of cyclopentane, cyclohexane, cycloheptane, 2-butene, isopentane, 1-pentene, 2-methyl-1-butene, trans-2-pentene, n-pentane, cis-2-pentene, 2-methyl-2-butene, 2,2-dimethylbutane, 2-methylpentane, 3-methylpentane, n-hexane and benzene. In a particularly preferred embodiment, the mixture G1 used in the process according to the invention comprises, as well as an olefin selected from the group consisting of cyclopentene, cyclohexene, cycloheptene, cyclooctene and mixtures thereof, at least one saturated hydrocarbon selected from the group consisting of cyclopentane, cyclohexane, cycloheptane, cyclooctene and mixtures thereof.

The at least one monocyclic olefin having from 4 to 20 carbon atoms, especially cyclopentene, is present in the mixture G1 generally in an amount of from 20 to 98% by weight, preferably from 30 to 80% by weight, more preferably from 40 to 60% by weight, based in each case on mixture G1.

In a preferred embodiment, the at least one further hydrocarbon, for example cyclopentane, is present in mixture G1 in an amount of from 2 to 80% by weight, preferably from 20 to 70% by weight, more preferably from 40 to 60% by weight, based in each case on mixture G1.

In a very particularly preferred embodiment, mixture G1 comprises from 20 to 98% by weight, preferably from 30 to 80% by weight, more preferably from 40 to 60% by weight, based in each case on mixture G1, of at least one monocyclic olefin having from 4 to 20 carbon atoms, especially cyclopentene, and from 2 to 80% by weight, preferably from 20 to 70% by weight, more preferably from 40 to 60% by weight, based in each case on mixture G1, of at least one further hydrocarbon, especially cyclopentane.

The present invention accordingly also relates to a process as described above, wherein a mixture G1 is used comprising from 20 to 98% by weight, preferably from 30 to 80% by weight, more preferably from 40 to 60% by weight, based in each case on mixture G1, of at least one monocyclic olefin having from 4 to 20 carbon atoms, and from 2 to 80% by weight, preferably from 20 to 70% by weight, more preferably from 40 to 60% by weight, based in each case on mixture G1, of at least one further hydrocarbon.

The content of other components in the mixture G1 is, for example, less than 15% by weight, preferably less than 12% by weight, preferentially less than 10% by weight, especially less than 8% by weight, more preferably less than 5% by weight.

In a further particularly preferred embodiment of the process according to the invention, the mixture G1 consists to an extent of at least 98% by weight, based on the total weight of the mixture G1, of hydrocarbons. In addition to the hydrocarbons, the mixture G1 may also comprise up to at most 5% by weight, preferably up to at most 2% by weight, of at least one further compound, for example a compound selected from the group consisting of aldehydes, ketones, epoxides and mixtures thereof, for example cyclopentanone, 3-methyl-2-butanone, epoxycyclopentane, 4-pentenal, acetone or mixtures thereof. These compounds may be present in the reaction mixture with the proviso that they do not disrupt the reaction of at least one monocyclic olefin having from 4 to 20 carbon atoms with the mixture G2.

In a preferred embodiment, the mixture G1 under the reaction conditions selected in accordance with the invention is gaseous, liquid or supercritical, preferably supercritical.

In a likewise preferred embodiment of the process according to the invention, a mixture G1 is used which consists to an extent of at least 90% by weight, preferably to an extent of at least 95% by weight, especially to an extent of at least 98% by weight, of $C_5$ hydrocarbons and hydrocarbons having more than 5 carbon atoms. In addition to cyclopentene, at least one further $C_5$ hydrocarbon may accordingly be present in G1, for example n-pentane and/or cyclopentane, or at least one hydrocarbon having more than 5 carbon atoms, for example cyclohexane, or a mixture of at least one further $C_5$ hydrocarbon and at least one hydrocarbon having more than 5 carbon atoms.

The present invention accordingly also describes a process as described above, wherein the mixture G1 comprises at least 98% by weight of $C_5$ hydrocarbons and hydrocarbons having more than 5 carbon atoms.

Particularly preferred hydrocarbons having more than 5 carbon atoms include the corresponding hydrocarbons already mentioned above in the context of the further hydrocarbons.

According to the invention, the mixtures G1 used are preferably those mixtures which are obtained in industrial scale processes. In the context of the present invention, preference is given here to mixtures which consist to an extent of at least 95% by weight, more preferably to an extent of at least 96% by weight and especially preferably to an extent of at least 97% by weight, of $C_5$ and $C_6$ or $C_5$ and $C_7$ or $C_5$ and $C_6$ and $C_7$ hydrocarbons.

The present invention accordingly also relates to a process as described above, wherein the mixture G1 consists to an extent of at least 95% by weight of $C_5$ and $C_6$ or $C_5$ and $C_7$ or $C_5$ and $C_6$ and $C_7$ hydrocarbons.

In the context of the present invention, the mixture G1 may comprise, as well as cyclopentene, at least one further $C_5$ hydrocarbon or at least one $C_6$ hydrocarbon or at least one $C_7$ hydrocarbon or a mixture of at least one further $C_5$ hydrocarbon and at least one $C_6$ hydrocarbon or a mixture of at least one further $C_5$ hydrocarbon and at least one $C_7$ hydrocarbon or a mixture of at least one further $C_5$ hydrocarbon and at least one $C_6$ hydrocarbon and at least one $C_7$ hydrocarbon.

According to the invention, the mixture G1 used may originate from any desired source. In the context of the present invention, the mixture G1 preferably originates at least partly from unconverted and recycled reactant of the process.

According to the invention, the mixture G1 originates at least partly from another source. In a preferred embodiment of the process according to the invention, the mixture G1 used is at least partly a hydrocarbon mixture which is obtained from a steamcracker or a refinery and comprises cyclopentene. In this connection, preference is given, for example, to $C_5$ cuts from steamcracker plants which comprise essentially only $C_5$ and $C_6$ hydrocarbons. Hydrocarbons having more than 6 carbon atoms are typically not present in the $C_5$ cuts obtained on the industrial scale. These $C_5$ cuts obtained on the industrial scale comprise, as well as cyclopentene, for example, 2-butene, isopentane, 1-pentene, 2-methyl-1-butene, trans-2-pentene, n-pentane, cis-2-pentene, 2-methyl-2-butene, cyclopentane, 2,2-dimethylbutane, 2-methylpentane, 3-methylpentane, n-hexane and benzene. In general, a $C_5$ cut from a steamcracker plant comprises cyclopentene in the range from 5 to 60% by weight and preferably in the range from 15 to 50% by weight. Such mixtures are advantageously purified further before they are used as mixture G1 in the process according to the invention.

The present invention therefore also describes a process as described above, wherein the mixture G1 comprises a mixture of $C_5$ and $C_6$ hydrocarbons to an extent of at least 95% by weight.

According to the invention, this mixture of essentially $C_5$ and $C_6$ hydrocarbons, which is preferably obtained as the $C_5$ cut from a steamcracker plant or from the partial hydrogenation of cyclopentadiene, may be used as such. The mixture of essentially C₅ and C₆ hydrocarbons is preferably subjected before the inventive reaction to a purification, in which, in turn, lower-boiling compounds compared to cyclopentene are removed preferentially. While all conceivable methods can be used here, preference is given to the distillative separation of the mixture.

More particularly, the present invention therefore also relates to a process as described above, wherein a cyclopentene-containing hydrocarbon mixture is used as a reactant to prepare cyclopentanone, the cyclopentene-containing hydrocarbon mixture being obtained either the C₅ cut of a steamcracker plant or that from the partial hydrogenation of cyclopentadiene.

The process according to the invention affords, through reaction of monocyclic olefins having from 4 to 20 carbon atoms with dinitrogen monoxide, the corresponding monocyclic ketones having from 4 to 20 carbon atoms. When olefins which comprise a carbon-carbon double bond are used, the process according to the invention affords monoketones. When olefins which comprise two or more carbon-carbon double bonds are used, it is possible in the context of the present invention that only one of the carbon-carbon double bonds reacts. However, it is also equally possible that two or more of the carbon-carbon double bonds react. In this case, the process according to the invention affords corresponding ketones which comprise one ketone functionality or two or more ketone functionalities.

For the case which is particularly preferred in accordance with the invention, that the mixture G1 used in the process according to the invention comprises a monocyclic olefin selected from the group consisting of cyclopentene, cyclohexene, cycloheptene, cyclooctene and mixtures thereof, a monocyclic ketone selected from the group consisting of cyclopentanone, cyclohexanone, cycloheptanone, cyclooctanone and mixtures thereof is obtained. Cyclopentanone (V), cyclohexanone (VI), cycloheptanone (VII) and cyclooctanone (VIII) are depicted below.

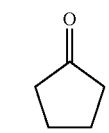

(V)

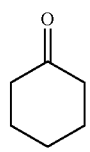

(VI)

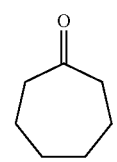

(VII)

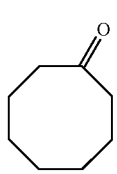

(VIII)

In a very particularly preferred embodiment, the process according to the invention serves to prepare cyclopentanone from cyclopentene and dinitrogen monoxide.

In the process according to the invention, a mixture G2 comprising at least dinitrogen monoxide is generally used.

According to the invention, the mixture G2 comprises at least 70% by volume of dinitrogen monoxide, for example from 70 to 100% by volume. The mixture G2 preferably comprises at least 75% by volume of dinitrogen monoxide, especially at least 80% by volume, preferably at least 85% by volume. The mixture G2 comprises preferably from 75 to 99% by volume of dinitrogen monoxide, more preferably from 80 to 95% by volume, especially preferably from 82 to 90% by volume, for example 83% by volume, 84% by volume, 85% by volume, 86% by volume, 87% by volume, 88% by volume or 89% by volume.

In a further embodiment, the present invention therefore also relates to the above-described process for preparing at least one monocyclic ketone having from 4 to 20 carbon atoms, comprising the reaction of a mixture G1 comprising at least one monocyclic olefin having from 4 to 20 carbon atoms with a mixture G2 comprising at least dinitrogen monoxide, wherein said reaction is performed adiabatically and the mixture G2 comprises at least 70% by volume of dinitrogen monoxide.

In a further embodiment, the present invention also relates to the above-described process for preparing at least one monocyclic ketone having from 4 to 20 carbon atoms, comprising the reaction of a mixture G1 comprising at least one monocyclic olefin having from 4 to 20 carbon atoms with a mixture G2 comprising at least dinitrogen monoxide, wherein said reaction is performed adiabatically and the mixture G2 comprises from 75 to 99% by volume of dinitrogen monoxide.

In principle, the mixture G2 comprising dinitrogen monoxide may originate from any desired source.

According to the invention, this mixture G2 is preferably liquefied and then used in liquid form. Dinitrogen monoxide or the gas mixture comprising dinitrogen monoxide can be liquefied by all processes known to those skilled in the art, especially through suitable selection of the pressure and of the temperature.

According to the invention, mixture G2 may comprise, as well as dinitrogen monoxide, also at least one further gas. In this context, essentially all gases are conceivable, provided that it is ensured that the inventive reaction of at least one monocyclic olefin having from 4 to 20 carbon atoms with dinitrogen monoxide is possible. Especially preferred are accordingly mixtures G2 which, as well as dinitrogen monoxide, comprise at least one inert gas. The term "inert gas", as used in the context of the present invention, refers to a gas which behaves inertly with regard to the reaction of dinitrogen monoxide with monocyclic olefins having from 4 to 20 carbon atoms and also with regard to dinitrogen monoxide under the reaction conditions. Inert gases include, for example, nitrogen, carbon dioxide, carbon monoxide, argon, methane, ethane and propane.

Equally, the mixture G2 may also comprise gases which do not behave as inert gases in the reaction of dinitrogen monoxide with monocyclic olefins having from 4 to 20 carbon atoms. Such gases include $NO_x$ or, for example, oxygen. The term "$NO_x$" as understood in the context of the present invention refers to all compounds $N_aO_b$ apart from dinitrogen monoxide ($N_2O$), where a is 1 or 2 and b is a number from 1 to 6. Instead of the term "$NO_x$", the term "nitrogen oxides" is also used in the context of the present invention. In such a case, preference is given to using those mixtures G2 whose content of these gases is at most 0.5% by volume, based on the total weight of the mixture G2.

The present invention accordingly also relates to the above-described process for preparing at least one monocyclic ketone having from 4 to 20 carbon atoms, comprising the reaction of a mixture G1 comprising at least one monocyclic olefin having from 4 to 20 carbon atoms with a mixture G2 comprising at least dinitrogen monoxide, wherein the mixture G2 comprises at most 0.5% by volume of oxygen or at most 0.5% by volume of nitrogen oxides or at most both 0.5% by volume of oxygen and 0.5% by volume of nitrogen oxides, based in each case on the total volume of the mixture G2. A value of, for example, 0.5% by volume refers here to a total content of all possible nitrogen oxides apart from dinitrogen monoxide of 0.5% by volume.

In principle, the composition of the mixtures in the context of the present invention can be determined in any manner known to those skilled in the art. The composition of the mixture G2 is preferably determined by gas chromatography in the context of the present invention. However, it can also be determined by means of UV spectroscopy, IR spectroscopy or by wet chemical means.

According to the invention, the mixture G2 is used especially in liquid or supercritical form. It is possible in accordance with the invention that the mixture G2 is subjected before the liquefaction to a treatment in order to reduce the concentration of inert and disruptive compounds in the mixture G2.

More particularly, it is possible in the context of the present invention to use mixtures G2 which are obtained from industrial scale processes. Should these mixtures G2, accordingly, comprise more than 0.5% by volume of oxygen and/or nitrogen oxides, they can generally be used in the process according to the invention. Preference is given to subjecting these mixtures G2, and also mixtures G2 of similar composition which are not obtained from industrial scale processes, to at least one purification step before use in the process according to the invention, in which the content of oxygen and/or nitrogen oxides is adjusted to at most 0.5% by volume.

A gas mixture G2 which is suitable in the context of the present invention comprises preferably from 50 to 99.0% by volume of dinitrogen monoxide, from 1 to 20% by volume of carbon dioxide and from 0 to 25% by volume of further gases. The % by volume stated are based in each case on the overall gas mixture G2. The sum of the individual components of the gas mixture G2 adds up to 100% by volume.

The gas mixture G2 preferably comprises from 60 to 95% by volume of dinitrogen monoxide, especially from 70 to 90% by volume and more preferably from 75 to 89% by volume of dinitrogen monoxide.

The gas mixture G2 may further comprise from 1 to 20% by volume of carbon dioxide. The gas mixture G2 preferably comprises from 5 to 15% by volume of carbon dioxide, especially from 6 to 14% by volume of carbon dioxide.

The gas mixture G2 preferably comprises from 0 to 25% by volume of further gases. The gas mixture G2 may comprise one or more further gases, the amount stated being based on the sum of the gases present.

Suitable processes for preparing such a gas mixture are known per se to those skilled in the art.

In the process according to the invention, the product stream obtained is preferably a reaction mixture G3 which comprises the at least one monocyclic ketone having from 4 to 20 carbon atoms, preferably cyclopentanone, and nitrogen.

In addition to these desired products, unconverted reactants and/or by-products, for example, are present in the mixture G3.

The at least one monocyclic ketone having from 4 to 20 carbon atoms obtained by the process according to the invention, preferably cyclopentanone, or the reaction mixture G3 which comprises the at least one monocyclic ketone having from 4 to 20 carbon atoms, preferably cyclopentanone, and is obtained by the process according to the invention, can in principle be processed further in the form obtained. According to the invention, the resulting mixture G3 can, however, also be worked up by all suitable processes for obtaining the at least one monocyclic ketone having from 4 to 20 carbon atoms, preferably cyclopentanone. Particular preference is given in accordance with the invention to distillative workup methods. In the context of the present invention, preference is given to effecting a further workup in a separation stage (B).

In a preferred embodiment, the present invention thus relates to a process as described above, at least comprising the following steps:

(A) reacting a mixture G1 comprising at least one monocyclic olefin having from 4 to 20 carbon atoms with a mixture G2 comprising at least dinitrogen monoxide under adiabatic conditions in order to obtain a reaction mixture G3 and (B) separating the at least one monocyclic ketone having from 4 to 20 carbon atoms from the reaction mixture G3 obtained in step (A).

Stage (A) of the process preferred in accordance with the invention and the preferred embodiments have already been described in detail above.

Stage (B) of the process, preferred in accordance with the invention, for preparing at least one monocyclic ketone having from 4 to 20 carbon atoms comprises separating the at least one monocyclic ketone having from 4 to 20 carbon atoms from the reaction mixture G3 obtained in step (A).

According to the invention, the separation stage (B) may comprise one or more purification steps.

The separation stage (B) preferably comprises at least one distillation, but preferably at least one one-stage evaporation, for example for removal of $N_2$ and unconverted dinitrogen monoxide, and at least one distillation, more preferably at least one one-stage evaporation and at least two distillation steps.

In a preferred embodiment of the process according to the invention, the mixture G3, in the separation stage (B), is first decompressed in at least one suitable vessel B1 to a pressure which is generally below the reaction pressure, for example to a pressure of from 1 to 20 bar, preferably from 14 to 18 bar. In a preferred embodiment, mixture G3 is cooled in a suitable heat exchanger before this decompression.

In a very particularly preferred embodiment of the process according to the invention, using the mixture G3 obtained directly from the inventive reaction, at least one reactant stream is first preheated as described above and then mixture G3 is decompressed to the pressure specified.

In a preferred embodiment of the present invention, the separation stage (B) comprises a one-stage evaporation in a vessel B1 and at least one distillation step in a suitable distillation column, preferably in a recycle column K1. In such an embodiment, after the decompression of the mixture G3 in vessel B1, a liquid mixture (G3f) and a gaseous mixture (G3g) are obtained.

According to the invention, the mixture G3g can preferably be cooled with one or more, preferably two, heat exchangers, for example to a temperature of not more than 50° C., preferably to a temperature below 5° C. and more preferably to a temperature below −10° C. The heat exchangers can be operated with all cooling media known to those skilled in the art, for example water, brine, etc. In a preferred embodiment of the process, the mixture G3g is cooled in a first heat exchanger by means of cooling water to a temperature of not more than 50° C. and, in a second heat exchanger, by means of brine, to a temperature of not more than 5° C., preferably of not more than −10° C. The cooling condenses a fraction of the gaseous mixture in each case. This condensed fraction is preferably recycled back into vessel B1 and combined with the mixture G3f to obtain a mixture G3f'. This method has the advantage that organic components which are present in the mixture G3g can be converted further. The resulting gaseous mixture G3g or the gaseous mixture obtained after passage through the heat exchangers can be removed by processes known to those skilled in the art.

In a preferred embodiment, the resulting liquid mixture G3f or the mixture G3f' is decompressed to a pressure of from 1 to 5 bar, for example 3 bar, and subjected to at least one distillation in order to separate the components present in mixture G3f or G3f' from one another.

The distillation performed with preference in separation stage (B) can be effected by all processes known to those skilled in the art. Temperatures, pressure, configuration of the distillation column(s), etc. are guided by the substances to be separated.

In separation stage (B) of the process according to the invention, the desired product, at least one ketone having from 4 to 20 carbon atoms, is preferably separated from unconverted reactant, any further components present in the reaction mixture and any by-products formed. In a particularly preferred embodiment of separation stage (B), the cyclopentanone product is separated from unconverted cyclopentene and any cyclopentane present in the reaction mixture.

In a particularly preferred embodiment of the process according to the invention, the mixture G3f or G3f' is distilled in separation stage (B) by using a recycle column K1 which has generally from 30 to 50 and preferably from 35 to 45 theoretical plates. The feed is generally in the middle part of the column. In a further preferred embodiment, for example, in the upper part of the recycle column K1 used in separation stage (B), unconverted monocyclic olefin having from 4 to 20 carbon atoms is obtained. Particular preference is given to obtaining cyclopentene in a side draw of column K1.

A suitable stream comprising unconverted monocyclic olefin having from 4 to 20 carbon atoms, more preferably cyclopentene, which has been distilled off can then, for example, be recycled and used as mixture G1 in the process according to the invention alone or after addition of a suitable mixture comprising monocyclic olefin having from 4 to 20 carbon atoms, more preferably cyclopentene.

In a particularly preferred embodiment, the unconverted monocyclic olefin having from 4 to 20 carbon atoms which has been removed in separation stage (B), for example in the side draw of column K1, is recycled into stage (A) of the process according to the invention, i.e. into mixture G1.

The present invention thus relates, in a preferred embodiment, to the above-described process, wherein monocyclic olefin having from 4 to 20 carbon atoms which has not been converted is removed in the separation stage (B).

In a further preferred embodiment, the present invention thus relates to the above-described process, wherein the unconverted monocyclic olefin having from 4 to 20 carbon atoms separated in the separation stage (B) is recycled into stage (A) of the process.

The distillation in separation stage (B) in the recycle column K1 is effected, for example, at a pressure of from 1.0 to 7.0 bar, preferably from 2.0 to 6.0 bar, for example from 3.5 to 5.0 bar.

The distillation in separation stage (B) in the recycle column K1 is effected, for example, at a temperature of from 80 to 200° C., preferably from 90 to 190° C. The temperature in the bottom of the column is, for example, from 150 to 200° C., preferably from 160 to 185° C.; the temperature above the bottom of the column is, for example, from 80 to 110° C., preferably from 90 to 105° C.

According to the invention, the at least one unconverted monocyclic olefin having from 4 to 20 carbon atoms can be obtained in different purity. According to the invention, the at least one unconverted monocyclic olefin having from 4 to 20 carbon atoms can be obtained, for example, in pure form, i.e. with a content of greater than 90% by weight, preferably 95% by weight.

In a further embodiment of separation stage (B), at least one unconverted monocyclic olefin having from 4 to 20 carbon atoms is obtained in a mixture with further hydrocarbons, for example saturated hydrocarbons, for example cyclopentane, for example as a mixture comprising from 20 to 98% by weight, preferably from 30 to 80% by weight, more preferably from 40 to 60% by weight, based in each case on the mixture, of at least one olefin having from 4 to 20 carbon atoms, especially cyclopentene, and from 2 to 80% by weight, preferably from 20 to 70% by weight, more preferably from 40 to 60% by weight, based in each case on the mixture, of at least one further hydrocarbon, for example a saturated hydrocarbon, especially cyclopentane. This mixture may comprise further components, for example hydrocarbons, product or by-product from stage (A) and/or linear olefins, up to a total content of up to 1.5% by weight, preferably up to 1.0% by weight, based in each case on the mixture.

In a further preferred embodiment of the separation stage (B), low-boiling components are obtained at the top of the recycle column K1, for example $C_5$ hydrocarbons such as n-pentane, 2-methyl-2-butene, cis-2-pentene and trans-2-pentene.

In a further embodiment of separation stage (B), the desired product, i.e. the at least one monocyclic ketone having from 4 to 20 carbon atoms, especially cyclopentanone, is obtained in the bottom of the recycle column K1, in a preferred embodiment with a purity of up to 95% by weight, preferably up to 92% by weight, based in each case on the bottom fraction.

According to the invention, the separation stage (B) can also be configured such that the at least one monocyclic ketone having from 4 to 20 carbon atoms, especially cyclopentanone, is obtained in a lower purity.

It is also possible in accordance with the invention that the separation stage (B), as well as the one-stage evaporation and the first distillation, preferably the distillation in a recycle column K1, comprises a further distillation. It is thus possible in accordance with the invention that the product can be purified further by distilling the at least one monocyclic ketone having from 4 to 20 carbon atoms, especially cyclopentanone, for example in one or more columns, preferably in two columns or more preferably in a dividing wall column K2.

According to the invention, the separation stage (B) comprises, in a preferred embodiment, a one-stage evaporation in a vessel B1, a distillation in a recycle column K1 and a further distillation in a distillation column K2, for example in a dividing wall column.

The product obtained in accordance with the invention from the distillation in the recycle column K1 is purified, for example, at a pressure of from 0.5 to 3 bar, preferably from 0.8 to 2 bar, for example from 1.0 to 1.2 bar.

The product obtained in accordance with the invention from the distillation in the recycle column K1 is purified, for example, at a temperature of from 100 to 200° C., preferably from 110 to 180° C., for example from 120 to 170° C.

For example, the product obtained in accordance with the invention from the distillation in the recycle column K1 is purified, for example, in a dividing wall column K2 at a pressure of from 0.5 to 3 bar, preferably from 0.8 to 2 bar, for example from 1.0 to 1.2 bar, and at a temperature of from 100 to 200° C., preferably from 110 to 180° C., for example from 120 to 170° C.

The present invention also relates to processes comprising at least steps (A) and (B), as described above, wherein the mixture G1 and/or G2 is preheated in step (A) to a temperature of from 170 to 270° C. before the reaction to give at least one monocyclic ketone having from 4 to 20 carbon atoms. Further details and preferred embodiments have already been specified above.

In a preferred embodiment, the present invention thus relates to a process as described above, at least comprising the following steps:

(A) reacting a mixture G1 comprising at least one monocyclic olefin having from 4 to 20 carbon atoms with a mixture G2 comprising at least dinitrogen monoxide under adiabatic conditions in order to obtain a reaction mixture G3 and (B) separating the at least one monocyclic ketone having from 4 to 20 carbon atoms from the reaction mixture G3 obtained in step (A), wherein the mixture G1 and/or G2 is preheated in step (A) to a temperature of from 170 to 270° C. before the reaction to give at least one monocyclic ketone having from 4 to 20 carbon atoms.

In a preferred embodiment of this process, the thermal energy needed for the preheating is withdrawn at least partly, preferably fully, from the product stream of the process according to the invention.

The process according to the invention is particularly advantageous for the oxidation of cyclic olefins with dinitrogen monoxide. However, the process is equally suitable in principle also for the oxidation of other compounds with dinitrogen monoxide, especially of compounds which comprise a CC double bond, for example noncyclic olefins or substituted olefins, for example enol ethers.

The invention will be illustrated in detail hereinafter by FIGURES and examples.

FIGURES

FIG. 1 shows an outline of a pilot plant in which the process according to the invention can be performed. The reference numerals have the following meanings:
1 Dinitrogen monoxide feed
2 Cyclopentene feed
3 Recycled unconverted cyclopentene
4 Offgas stream
5 Low boiler purge
6 Low boilers
7 High boilers
8 Cyclopentanone product
9 Condensate
M Mixer
R Reactor
WT Heat exchanger/partial condenser
B1 Phase separation vessel
K1 Recycle column
K2 Fine purification column(s)

Figure 2:
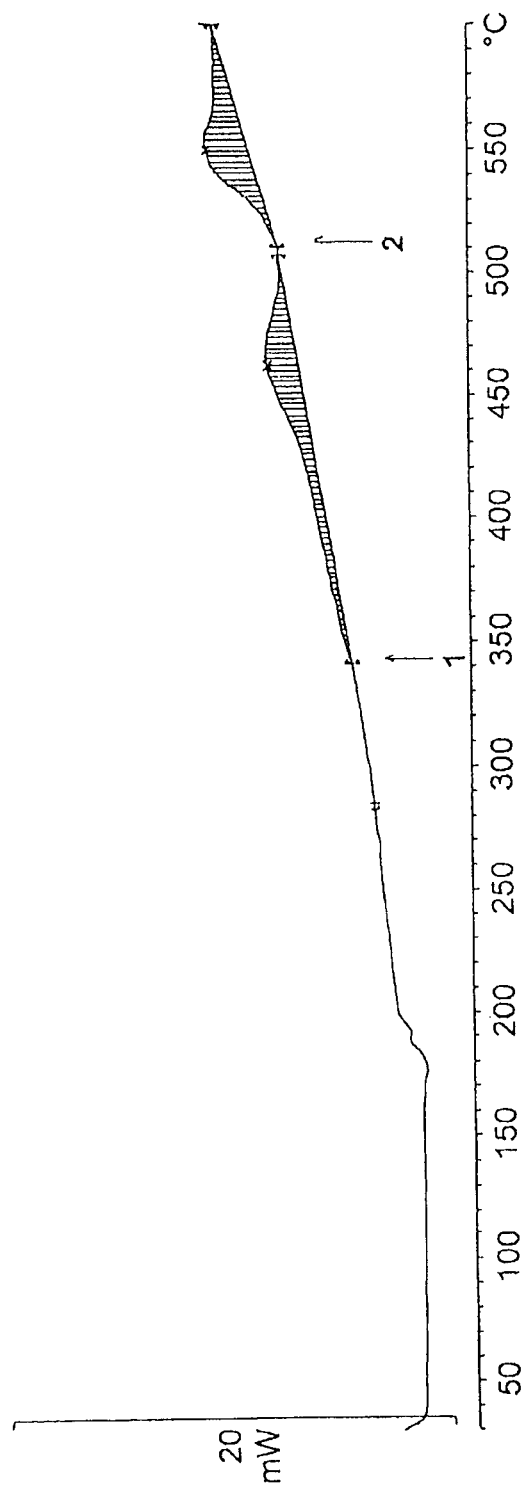
Figure 3:
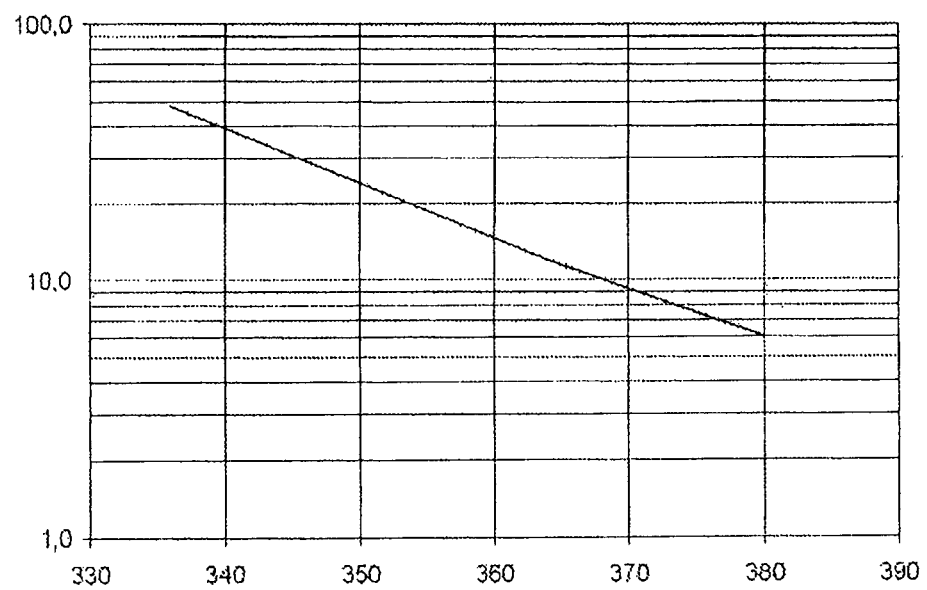

FIG. 2 shows the heat development (in the unit mW, plotted on the northing axis=y axis), plotted over the temperature (in the unity ° C., plotted on the easting axis=x axis), obtained by DSC-experiment according to example 5. The area overstretched by the northing axis is 20 mW. The classification of the easting axis is carried out in steps of 10° C. at which the easting axis starts at 30° C. and ends at 600° C. Regarding the procedure of the experiment, reference is made to the corresponding embodiment of example 5. The reference numerals have the following meanings:
1 lowest onset temperature for the reactor output (345° C.) for the beginning decomposition reaction
2 onset temperature (515° C.) for the second reaction FIG. 3 shows the estimated adiabatic induction according to example 6, as a function of temperature. On the casting axis (=x axis) the temperature is plotted in ° C., on the northing axis (=y axis) the adiabatic induction time is plotted in hours. For determination of the estimated induction time, reference is made to example 6.

EXAMPLES

Example 1

The pilot plant according to FIG. 1 is used.

Through stream 2, the fresh cyclopentene feed is metered in at 116.4 g/h. This originates from the distillation of a C$_5$ cut of a steamcracker and has the following composition (% by weight): cyclopentene (approx. 95.1%), cyclopentane (approx. 3.4%), 2-methyl-2-butene (approx. 1.2%).

This stream 2 is first mixed with stream 3 (return cyclopentene) in order to obtain a stream which has the following composition: cyclopentene (approx. 46.3%), cyclopentane (approx. 51.9%), 2-methyl-2-butene (approx. 0.9%), 2,2-dimethylbutane (approx. 0.81%).

This stream is then metered into the reactor with a metering pump (flow rate: approx. 2076 g/h). Through stream 1, liquid dinitrogen monoxide (dinitrogen monoxide content >99.8% by volume, from Messer Griesheim) is metered into the reactor at approx. 74 g/h. The molar cyclopentene:dinitrogen monoxide ratio in the reactor feed is 0.11 mol/mol. The reactor consists of a tube (external diameter=60.3 mm, wall thickness=2.4 mm, length=3500 mm) filled with thin-wall stainless steel Raschig rings (6×6×0.3 mm). To determine the longitudinal temperature profile, a thermowell of external diameter 16 mm was installed along the reactor axis and provided with a 15-point thermocouple. The reaction volume is (minus random packings and thermowell), including connecting pieces, approx. 7 l in total. The pressure in the reactor is adjusted to 100 bar with a suitable pressure-retaining device at the reactor outlet.

The tube is provided with an insulating jacket composed of a nanoporous inorganic foam from Microtherm (two layers of thickness in each case 50 mm). In order to reduce the heat losses even further, a three-part trace-heating system is also installed on the outside of the insulating jacket, and is adjusted to (v.u.) 256, 275 & 317° C. (preliminary tests without addition of dinitrogen monoxide ensured that the heat losses are only very low. When the reactor inlet temperature is approx. 260° C., the remaining heat losses lead to a cooling by merely 3° C. up to the reactor outlet). The residence time distribution of the reactor was determined in a preliminary test with a radioactive marker. The Bodenstein number determined has the value of 117, which corresponds to an equivalent stirred tank cascade with 58 stirred tanks.

The feed stream is fed into the reactor from the bottom via a heated inlet nozzle, in which the feed stream is also heated. At a reactor inlet temperature of 239.5° C. (measured at the lowermost thermocouple in the thermowell), the cyclopentene conversion in straight pass is 11% and the dinitrogen monoxide conversion approx. 96%. The selectivity for cyclopentanone based on cyclopentene is 96.8%. The reactor output has a temperature of 295° C. The adiabatic temperature increase is thus 55.5° C. The reactor output is decompressed to 1 bar in a two-stage decompression and cooled. The gaseous components are removed and, in an aftercooler (which is operated at +5° C.), the hydrocarbons present therein are very substantially condensed out.

The liquid phase, which of the liquid reactor output and of the condensate, is separated in a distillation column (bubble-cap tray column with 20 trays and liquid side draw). The bottom product obtained is 138.7 g/h of a stream with the following composition (% by weight): cyclopentanone (approx. 95.3%), cyclopentane (approx. 0.8%), 4-pentenal (approx. 1.3%), cyclopentene oxide (approx. 0.37%), cyclopentene dimers (approx. 0.53%), cyclopentene (approx. 0.08%). The side draw product which comprises 45.6% cyclopentene is recycled as stream 3 to the reactor.

The combined gas phases (from decompression & top of the recycle column, approx. 47.7 l/h) have the following composition: $N_2$ (81.1% by volume), dinitrogen monoxide (2.46% by volume), cyclopentene (0.96% by volume), cyclopentane (0.48% by volume).

Example 2

Example 1 was repeated, with the difference that a reactor inlet temperature of 255.4° C. was selected. In this case, the cyclopentene conversion in straight pass was approx. 12% and the dinitrogen monoxide conversion 99%. The reactor output has an outlet temperature of 313° C. The adiabatic temperature increase is thus 57.6° C. The selectivity for cyclopentanone based on cyclopentene is 94.8%.

Example 3

Example 1 was repeated, with the difference that a reactor inlet temperature of 225.9° C. was selected. In this case, the cyclopentene conversion in straight pass was 9.7% and the dinitrogen monoxide conversion 83%. The reactor output has an outlet temperature of 277° C. The adiabatic temperature increase is thus 51.1° C. The selectivity for cyclopentanone based on cyclopentene was 95.2%.

Example 4

In order to demonstrate the fine purification of cyclopentanone, outputs from example 1, example 2 and other analogous experiments were collected and distilled in a laboratory dividing wall column. The column had an internal diameter of 43 mm and a height of 2.5 m and was equipped with a structured packing (Montt A3 1000). The number of theoretical plates was determined with a test mixture in preliminary tests, and was 53 theoretical plates at the F factor used. The dividing wall was inserted in the region between 820 and 2100 mm above the lower edge of the structured packing, and divided the column exactly in the middle. Feed and side draw were both placed 1300 mm above the lower edge of the structured packing but on different sides of the dividing wall.

The column feed (17.5 kg in total) had the following composition (% by weight): cyclopentanone (95.6), cyclopentane (0.8), cyclopentene (0.08), 4-pentenal (1.3), cyclopentene oxide (0.4), isopropyl methyl ketone (0.2), diethyl ketone (0.03), 2,2-dimethylbutane (0.005), as well as other components such as cyclopentene dimers, cyclopentylcyclopentanone, cyclopentenylcyclopentanones, cyclobutanecarbaldehyde, cyclopropylacetaldehyde and other unidentified secondary components.

The distillation was performed at standard pressure with a feed rate of 0.33 kg/h and a reflux ratio of 90. In the side draw, cyclopentanone was obtained with a purity of 99.89%. The distillation yield was 99.5% (based on cyclopentanone).

Example 5

A sample (18.3 mg) of the already decompressed and degassed reactor output from example 1 was sealed under a nitrogen atmosphere in a pressure-resistant V4A crucible and, in a suitable apparatus (Mettler TA 8000), a differential scanning calorimetry (DSC) test with a temperature ramp of 1 K./min was carried out. The result is shown in FIG. 2.

In the diagram, the evolution of heat in mW (y axis) is plotted against the temperature in ° C. (x axis).

The lowest onset temperature for the reactor output determined therefrom is accordingly 345° C. for the first onset of decomposition reaction (in FIG. 2: 1). The measurement for the heat released in the first decomposition reaction gives rise to a value of 263.7 J/g. For the second reaction, an onset temperature of 515° C. is found (in FIG. 2: 2). For the second reaction, the measurement of the heat released in the decomposition reaction gives rise to a value of 208.7

Example 6

Example 5 was repeated with different temperature ramps of 0.3 K/min and 2.5 K/min. The data obtained, together with the data from example 5, were used for the derivation 20 of formal decomposition kinetics. For the evaluation, only the data in the range between 360 and 520° C. were used, and were analyzed with the NETZSCH THERMOKINETICS program. The best fit to the data measured was fitted with a Prout-Tompkins rate equation, which was fitted to the data of the DSC tests by multivariant nonlinear regression. On the basis of the formal kinetic model, assuming a constant heat capacity of 2 $J \cdot g^{-1} \cdot K^{-1}$ the adiabatic induction time of the decomposition reaction was calculated for the range from 336 to 380° C. (to this end, the NETZSCH THERMSIM program was used). The adiabatic induction time estimated thereby, as a function of temperature, is shown in FIG. 3. The temperature in ° C. is plotted on the x axis and the adiabatic induction time in hours on the y axis.

The invention claimed is:
1. A continuous process for preparing at least one monocyclic ketone having from 4 to 20 carbon atoms which comprises reacting a mixture G1 at a temperature of 170 to 340° C. comprising at least one monocyclic olefin having from 4 to 20 carbon atoms with a mixture G2 comprising at least dinitrogen monoxide, which comprises performing said reaction adiabatically, and the mixture G1 and/or G2 is preheated to a temperature of from 170 to 270° C. before the reaction to give at least one monocyclic ketone having from 4 to 20 carbon atoms, wherein the thermal energy needed to preheat mixture G1 and/or G2 is withdrawn at least partly from the product stream of the process.

2. The process according to claim 1, wherein the thermal energy needed to preheat mixture G1 is withdrawn at least partly from the product stream of the process.

3. The process according to claim 1, wherein a mixture G1 is used comprising from 20 to 98% by weight, based in each case on mixture G1, of at least one monocyclic olefin having from 4 to 20 carbon atoms, and from 2 to 80% by weight, based in each case on mixture G1, of at least one further hydrocarbon.

4. The process according to claim 3, wherein a mixture G1 is used comprising from 30 to 80% by weight, based in each case on mixture G1, of at least one monocyclic olefin having from 4 to 20 carbon atoms, and from 20 to 70% by weight, based in each case on mixture G1, of at least one further hydrocarbon.

5. The process according to claim 4, wherein a mixture G1 is used comprising from 40 to 60% by weight, based in each case on mixture G1, of at least one monocyclic olefin having from 4 to 20 carbon atoms, and from 40 to 60% by weight, based in each case on mixture G1, of at least one further hydrocarbon.

6. The process according to claim 1, wherein the mixture G1 comprises at least one monocyclic olefin selected from the group consisting of cyclopentene, cyclohexene, cycloheptene, cyclooctene and mixtures thereof.

7. The process according to claim 1, wherein the molar ratio between dinitrogen monoxide and the at least one monocyclic olefin in the reaction is between 0.02 and 0.3.

8. The process according to claim 1, wherein the adiabatic temperature increase in the reactor is between 10 and 140° C.

9. The process according to claim 1, wherein the adiabatic temperature increase in the reactor is between 25 and 100° C.

10. The process according to claim 1, wherein the reactor outlet temperature is below the onset temperature for the decomposition of the product mixture.

11. The process according to claim 1, wherein the reactor outlet temperature is at least 10 K below the temperature at which the adiabatic induction time of the product mixture is 24 hours.

12. The process according to claim 1, which is performed at a reaction pressure of from 60 to 500 bar.

13. The process according to claim 1, wherein the mixture G2 comprises at least 75% by volume of dinitrogen monoxide.

14. The process according to claim 1, wherein the conversion based on dinitrogen monoxide is from 80 to 100%.

15. The process according to claim 1, at least comprising the following steps:
(A) reacting a mixture G1 comprising at least one monocyclic olefin having from 4 to 20 carbon atoms with a mixture G2 comprising at least dinitrogen monoxide under adiabatic conditions in order to obtain a reaction mixture G3 and
(B) separating the at least one monocyclic ketone having from 4 to 20 carbon atoms from the reaction mixture G3 obtained in step (A).

16. The process according to claim 15, wherein unconverted monocyclic olefin having from 4 to 20 carbon atoms is removed in the separation stage (B).

17. The process according to claim 16, wherein the unconverted monocyclic olefin having from 4 to 20 carbon atoms separated in the separation stage (B) is recycled into stage (A) of the process.

18. The process according to claim 1, wherein at least one part of the product stream is contacted with at least a portion of mixture G1 in a heat exchanger.

* * * * *